United States Patent
Lesens et al.

(10) Patent No.: US 6,399,124 B1
(45) Date of Patent: Jun. 4, 2002

(54) FROZEN DESSERT CONTAINING LACTIC ACID BACTERIA

(75) Inventors: Corinne Lesens, Beauvais (FR); Andrea M. Pfeifer, Saint-Legier; Florence Rochat, Montreux, both of (CH)

(73) Assignee: Nestec SA, Vevey (CH)

( * ) Notice: Subject to any disclaimer, the term of this patent is extended or adjusted under 35 U.S.C. 154(b) by 0 days.

(21) Appl. No.: 09/472,931

(22) Filed: Dec. 27, 1999

Related U.S. Application Data

(63) Continuation-in-part of application No. PCT/EP98/03721, filed on Jun. 12, 1998.

(30) Foreign Application Priority Data

Jul. 5, 1997 (EP) .............................. 97111382

(51) Int. Cl.⁷ ............................ A23C 9/123; A23G 9/00
(52) U.S. Cl. .......................... 426/61; 426/101; 426/565
(58) Field of Search .......................... 426/61, 101, 302, 426/305, 306, 565

(56) References Cited

U.S. PATENT DOCUMENTS

| | | | |
|---|---|---|---|
| 4,435,389 A | | 3/1984 | Mutai et al. ................ 424/181 |
| 5,527,556 A | * | 6/1996 | Frippiat et al. ............ 426/573 |

FOREIGN PATENT DOCUMENTS

| | | | |
|---|---|---|---|
| DE | 154424 | | 3/1982 |
| EP | 0 199 535 B1 | | 10/1986 |
| EP | 0 307 523 | | 3/1989 |
| EP | 0 307 656 1 | | 4/1991 |
| EP | 0 438 201 A1 | | 7/1991 |
| EP | 0 727 817 0 | | 10/1995 |
| EP | 0 726 272 A2 | | 8/1996 |
| EP | 0 577 904 B1 | | 5/1997 |
| EP | 0 915 453 5 | | 6/1997 |
| EP | 0 577 903 B1 | | 12/1997 |
| JP | 03049670 | | 3/1991 |
| JP | 04349868 | | 12/1992 |
| JP | 07067575 | | 3/1995 |
| SU | 1374465 | | 6/1989 |
| WO | WO 94/12541 | | 6/1994 |
| WO | 95/01732 | * | 1/1995 |
| WO | WO 95/17103 | | 6/1995 |
| WO | WO 97/29762 | | 8/1997 |

OTHER PUBLICATIONS

Johnson et al., "Taxonomic Study of the *lactobacillus acidophilus* Group, with Recognition of *Lactobacillus gallinarum* sp. nov. and *Lactobacillus johnsonii* sp. nov. Synonymy of *Lactobacillus acidophilus* Group A3", International Journal of Systematic Bacteriology, vol. 42, p. 487–491 (Jul. 1992.)

T. Nakakuki, "Development of gentiooligosaccharide–containing syrups and their properties", (Feb. 1996), abstract.

Modler et al., Using Ice Cream as a Mechanism to Incorporate Bifidobacteria and Fructooligosaccharides into the Human Diet,Food Science & Technology, XP002051107 (Aug. 1990).

Goff et al., "Bifidobacteria, Fructooligosaccharides and Ice Cream", ,Food Science & Technology, XP002051108, Jul. 1996.

\* cited by examiner

*Primary Examiner*—Keith Hendricks
(74) *Attorney, Agent, or Firm*—Winston & Strawn

(57) ABSTRACT

Frozen dessert based on an ice cream containing lactic acid bacteria, the said ice cream being coated over all or part of its surface with, and/or placed in, and/or between, an edible support, characterized in that the support is substantially free of lactic acid bacteria, and in that it comprises fermentable fibers specifically promoting the growth, in the intestinal tract, of the lactic acid bacteria contained initially in the ice cream. The invention also relates to the combined use of lactic acid bacteria and prebiotic fibers, for the preparation of a frozen composition in which the lactic acid bacteria and the fibers are not substantially in contact, for the treatment and/or the prevention of gastrointestinal disorders, for strengthening the human immune system, or for increasing the absorption of minerals.

26 Claims, No Drawings

US 6,399,124 B1

FROZEN DESSERT CONTAINING LACTIC ACID BACTERIA

CROSS-REFERENCE TO RELATED APPLICATIONS

This application is a continuation-in-part of the U.S. National Stage of International Application No. PCT/EP98/03721, filed Jun. 12, 1998,the content of which is expressly incorporated herein by reference thereto.

FIELD OF THE INVENTION

The present invention relates to frozen desserts containing lactic acid bacteria and dietary fibers, and to the beneficial effects, on human health, by consumption of such frozen desserts containing lactic acid bacteria and dietary fibers.

BACKGROUND OF THE INVENTION

Although lactic acid bacteria are generally known to have beneficial effects on human health, only some categories of lactic acid bacteria, called probiotic bacteria, are really capable of adhering to human intestinal cells, of excluding pathogenic bacteria on human intestinal cells, and/or of acting on the human immune system by allowing it to react more strongly to external aggression. Among the lactic acid bacteria recognized as such, there may currently be distinguished the strains Lactobacillus plantarum 299, Lactobacillus rhamnosus ATCC53103, Lactobacillus acidophilus CNCM I-1225, Bifidobacterium breve CNCM I-1226, Bifidobacterium infantis CNCM I-1227 and Bifidobacterium longum CNCM I-1228 (EP577904; EP577903; EP199535; U.S. Pat. No. 5,591,428; Gut, 35 483–489, 1994; J. of Dairy Science, 78, 491–497, 1995; Applied Env. Microb., 59, 4121–4128, 1993), for example.

The use of the beneficial properties of lactic acid bacteria has not escaped the area of frozen desserts. U.S. Pat. No. 5,112,626 (Pillsbury) indeed proposes preparing a yoghurt fermented by Lactobacillus bulgaricus and Streptococcus thermophilus, and then whipping it and freezing it. Likewise, Hekmat et al. propose preparing ice creams which have been fermented by lactic acid bacteria known to be particularly beneficial for human health (J. Dairy Science, 75, 1415–1422, 1992), for example.

Prebiotic dietary fibers are generally of a protein or saccharide nature which behave like growth factors for certain lactic acid bacteria. The literature relating to these fibers is abundant and there may be mentioned, by way of example, Patents EP726272 (Hayashibara Seibutsu KK), U.S. Pat. No. 4,435,389 (Yakult Honsha KK), and the articles by T. Nakakuti (Foods and Food Ingredient J. of Japan, 167, 116–121, 1996) and by Playne et al. (Bulletin of the IDF 313, Group B42, Annual Session of September 95, Vienna).

The simultaneous use of lactic acid bacteria and of dietary fibers has also been proposed for the preparation of frozen desserts.

Thus, M. W. Modler et al. report that an ice cream containing bifidobacteria and fructooligosaccharides is of remarkable interest to human health (Cult. Dairy Prod. J., 25, p. 4–9, 1990; Canadian Dairy, 75, p. 10, 1996). Likewise, EP307523 (Yakult Honsha KK) reports that a fermented milk containing prebiotic fibers may be packaged in the form of an ice cream and thus be used to treat certain gastrointestinal disorders.

However, bringing the dietary fibers into contact with the lactic acid bacteria has significant disadvantages, having a direct effect on human health. These disadvantages are of various types, and relate in particular to the premature destruction of the fibers during the preparation and storage of the dessert, and to the poor conditions in vivo in which the biological activity of these fibers develops, for example.

Up until now, these disadvantages have not been reported, nor in fact any product as defined in the present invention. The present invention is thus intended to potentiate the beneficial effect, on human health, of frozen desserts containing lactic acid bacteria and dietary fibers.

SUMMARY OF THE INVENTION

To this effect, the invention relates to a frozen dessert based on an ice cream containing lactic acid bacteria, the said ice cream being coated over all or part of its surface with, and/or placed in, and/or between, an edible support, characterized in that the support is substantially free of lactic acid bacteria, and in that it comprises fermentable dietary fibers specifically promoting the growth, in the intestinal tract, of the lactic acid bacteria contained in the ice cream.

The subject of the invention is also the combined use of lactic acid bacteria and prebiotic fibers, for the preparation of a frozen composition in which the lactic acid bacteria and the fibers are not substantially in contact, for the treatment and/or prevention of gastrointestinal disorders, for strengthening the human immune system, or for increasing the absorption of minerals.

DETAILED DESCRIPTION OF THE INVENTION

The ice cream according to the invention may have all the compositions chosen by persons skilled in the art, as long as it has an overrun of 20% to 200% by volume, for example.

Preferably this cream comprises, after overrun has been obtained and after freezing, more than $10^6$ cfu/g of lactic acid bacteria, it being possible for the said bacteria to be chosen from the species Lactococcus lactis, in particular L. lactis subsp. cremoris and L. lactis subsp. lactis biovar diacetylactis; Streptococcus thermophilus; the groups of acidophilic bacteria consisting of Lactobacillus acidophilus, Lactobacillus crispatus, Lactobacillus amylovorous, Lactobacillus gallinarum, Lactobacillus gasseri and Lactobacillus johnsonii; Lactobacillus rhamnosus, Lactobacillus brevis; Lactobacillus fermentum; Lactobacillus plantarum; Lactobacillus helveticus; Lactobacillus casei in particular L. casei subsp. casei and L. casei subsp. rhamnosus; Lactobacillus delbruckii in particular L. delbruckii sbp. lactis and L. delbruckii sbp. bulgaricus; the bifidobacteria, in particular Bifidobacterium infantis, Bifidobacterium breve, Bifidobacterium longum; and finally Leuconostoc mesenteroides in particular L. mesenteroides subsp. cremoris, for example (Bergey's Manual of Systematic Bacteriology, vol 2, 1986; Fujisawa et al., Int. Syst. Bact, 42, 487–491, 1992).

The probiotic lactic acid bacteria are, to this effect, of particular interest within the framework of the present invention. These bacteria are in fact capable of adhering to human intestinal cells, of excluding pathogenic bacteria on human intestinal cells, and/or of acting on the human immune system by allowing it to react more strongly to external aggression (immunomodulatory capacity), for example by increasing the phagocytosis capacities of the granulocytes derived from human blood (J. of Dairy Science, 78, 491–497, 1995: immunomodulatory capacity of the strain La-1 which has been deposited under the Treaty of Budapest at the Collection Nationale de Culture de Microorganisme (CNCM), 25 rue du docteur Roux, 75724 Paris, where it was attributed the deposit number CNCM I-1225).

By way of example, the probiotic strain *Lactobacillus acidophilus* CNCM I-1225 (see EP577904, Société des Produits Nestlé) may be used. This strain was recently reclassified among the *Lactobacillus johnsonii* strains, following the new taxonomy proposed by Fujisawa et al., which is now authoritative as regards the taxonomy of acidophilic lactobacilli (Int. J. Syst. Bact., 42, 487–791, 1992). Other probiotic bacteria are also available, such as those described in EP199535 (Gorbach et al.), U.S. Pat. No. 5,296,221 (Mitsuoka et al.), U.S. Pat. No. 5,556,785 (Institut Pasteur), or U.S. Pat. No. 5,591,428 (Probi AB), for example.

Many methods are available to persons skilled in the art for preparing a whipped ice cream comprising live lactic acid bacteria. To this effect, the processes described in DD154424, EP438201, SU1374465, FR2423163, NL9000101, U.S. Pat. No. 4,293,573, U.S. Pat. No. 4,308,287 and U.S. Pat. No. 5,112,626 may be incorporated by way of preference into the description of the present invention, persons skilled in the art being capable of adapting them in order to carry out the present invention, for example.

Certain preparation processes are, however, more suitable for ensuring a large number of live lactic acid bacteria in the aerated ice cream.

To this effect, a neutral gas may be incorporated during whipping, such as $CO_2$ or nitrogen, alone or as a mixture, so as to protect the lactic acid bacteria which are sensitive to oxygen, for example.

It is also possible to aerate the cream to an overrun of 130–200% by volume, and then to incorporate therein a milk fermented by lactic acid bacteria in order to reach a final overrun of the order of 80–150% by volume, for example.

In order to ensure a large number of live lactic acid bacteria in the aerated ice cream, the temperature at the outlet of the dasher is also considered to be an important parameter. For example, a cream aerated to an overrun of about 95% and cooled to about −3° C. at the outlet of the dasher contains significantly more live bacteria ($10^7$ cfu/g) than a cream aerated to an overrun of about 95% and cooled to about −6° C. which contains about 2 to 10 times less (5 to 1 times $10^6$ cfu/g). This difference is maintained after hardening of the ice cream and after 1, 3 and 6 months of storage at −30° C.

Another advantage which is incidental to the addition of a fermented milk during the manufacture of an aerated ice cream is to develop a very smooth, very creamy texture even if the fat level is less than or equal to 8%, and to develop a flavor of lactic origin having a buttery note. This creamy texture is maintained, for several weeks, during accelerated aging tests (successive temperature cycles spread over 24 h corresponding to steps at −10° C., −20° C. and −30° C., and then at −30° C., −20° C. and −10° C.). The aerated ice cream containing a fermented milk also has a very good resistance in the melting test (measurement of the weight of molten ice cream as a function of time, when the ice cream is kept in a chamber at +20° C.). For example, after more than two hours of melting test, only 40% to 50% of the ice cream is in liquid form, the remainder being maintained in the form of a foam. Furthermore, the size of the ice crystals, directly influencing the "smooth" character of the ice cream, also varies very slightly (about 1 to 10 $\mu$m for the mean diameter of the crystals) between the beginning and the end of the accelerated aging. The advantage of this good resistance in the melting test and of maintaining the creamy texture during storage and of the low variation in the size of the ice crystals during accelerated aging is, for example, to be able to fill an edible support such as a wafer in the shape of a cone, and to form a "flame" of the order of 50 mm in height, and then to be able to retain this "flame" shape during storage.

In an alternative to the present invention, it may be chosen to add to the cream encapsulated lactic acid bacteria, dried or otherwise, for example according to one of the techniques described hereinafter.

The frozen dessert according to the present invention comprises, moreover, a support with which is coated, or in which or between which is placed, the ice cream according to the invention. This support is substantially free of lactic acid bacteria, which means that lactic acid bacteria are not deliberately introduced into its composition. This support contains, in addition, fibers which are not or are only slightly digested in the stomach and the intestinal tract, but which may, nevertheless, be specifically fermented by the lactic acid bacteria present in the ice cream, thus making it possible to restore or to promote an intestinal flora which is high in beneficial lactic acid bacteria.

These fibers may be of a protein or saccharide nature, chosen, for example, from vegetable pectins, chito-, fructo-, gentio-, galacto-, isomalto-, manno- or xylo-oligosaccharides, or soya bean, *Polymnia sonchifolia*, artichoke, onion or asparagus oligosaccharides, or resistant starches, or products high in β-glucans such as an oats concentrate, for example (Playne et al.; Fukai et al., Soil Sci. Plant Nutr., 39, 567–571, 1993).

The preferred pectins are polymers of α-1,4-D-galacturonic acid having a molecular weight of the order of 10 to 400 kDa, which can be purified from carrots or tomatoes, for example (JP60164432). The preferred galacto-oligosaccharides comprise a saccharide part consisting of 2 to 5 repeating units of structure {-α-D-Glu-(1→4)-β-D-Gal-(1→6)-} (Yakult Honsa Co., Japan). The preferred fructoo-ligosaccharides are inulin-oligofructoses extracted from chicory which may comprise, for example, 1-9 repeating units of structure {-β-D-Fru-(1→2)-β-D-Fru-(1→2)-} (WO94/12541; Raffinerie Tirlemontoise S.A., Belgium), or oligosaccharides synthesized from sucrose units which may comprise, for example, a sucrose part consisting of 2 to 9 repeating units of structure {-α-D-Glu-(1→2)-β-D-Fru- (1→2)-} (Meiji Seika Kasiha Co., Japan). The preferred maltooligosaccharides comprise a saccharide part consisting of 2 to 7 repeating units of structure {-α-D-Gal-(1→4)-} (Nihon Shokuhin Kako Co., Japan). The preferred isomaltoses comprise a saccharide part consisting of 2 to 6 repeating units of structure {-α-D-Glu-(1→6)-} (Showa Sangyo Co., Japan). The preferred gentiooligosaccharides comprise a saccharide part consisting of 2 to 5 repeating units of structure {-β-D-Glu-(1→6)-} (Nihon Shokuhin Kako Co., Japan). Finally the preferred xylooligosaccharides comprise a saccharide part consisting of 2 to 9 repeating units of structure {-β-xyl-(1→4)-} (Suntory Co., Japan), for example.

The quantity of fibers in the dessert according to the invention depends on their capacity to promote the development of lactic acid bacteria. As a general rule, the support may contain from 0.1 to 20% of such fibers (by weight relative to the dry matter content). In other words, the dessert may comprise at least 103 cfu of lactic acid bacteria per g of fibre, preferably $10^4$ to $10^7$ cfu/g of fibre, for example.

Moreover, the dessert may be designed so as to be able to potentially provide up to a maximum of 10 g of fibre per dessert, higher quantities of fibers indeed inducing an unpleasant feeling of heaviness in the stomach (Bouhnik et al., Cah. Nutr. Diet., 6, 418–422, 1991; Ito et al., Microb. Ecol. Health Dis., 3, 285–292, 1990).

The novelty of the present invention consists particularly in the fact that the lactic acid bacteria are not substantially in contact with the fibers, which avoids an untimely fermentation of the fibers during the preparation of the dessert, in particular when the cream is fermented during the process for the manufacture of the dessert according to the invention (see Example 2).

Moreover, it has been observed that the more solid concentrate of fibers the diet contains, the more the intestinal transit of these fibers is retarded, with a corresponding positive influence on the development of the lactic acid bacteria in the intestine. During a study on human volunteers, it has thus been demonstrated that digestive disorders, probably linked to a bacterial fermentation which is excessive and limited over time, are more marked when subjects are fed with fructooligosaccharides (FOS) and lactic acid bacteria packaged in an oral liquid solution, and this in comparison with the results obtained with a diet containing the same quantity of FOS packaged in the presence of solid foods and lactic acid bacteria.

In summary, the more concentrated the fibers in the dessert according to the invention, for example by placing them in a solid support distinct from the ice cream (coating, such as a non-aerated ice cream coating, wafer, and the like), the more a bacteria fermentation is promoted in the intestine which is prolonged and sufficient to satisfy the needs of the human body.

Another incidental problem solved by the present invention consists in the fact that certain fibers may be easily degraded by the acidic pH developed by the lactic acid bacteria. This degradation may be observed when it is desired to ferment a cream containing these fibers, or alternatively when an ice cream containing fibers and lactic acid bacteria is subjected to an accelerated ageing treatment.

Once again, the separation of the fibers from the fermented ice cream therefore indeed makes it possible to potentiate the beneficial effect of the lactic acid bacteria on human health.

In a first embodiment of the invention, the edible support may be a composition traditionally serving to coat an ice cream. The coating may be conventionally carried out by spraying, dipping or moulding, for example. As a guide, the coating techniques and compositions described in U.S. Pat. No. 4,985,263, WO95/21536 and FR2680635 are incorporated by reference into the description of the present invention.

Preferably, at least part of the coating was fermented by lactic acid bacteria, and then pasteurized so as to kill all the lactic acid bacteria and to preserve only the textural properties provided by them. In this context, it is possible to use lactic acid bacteria producing texturing polysaccharides, in particular those described in EP95201669.9 and EP96201535.0. Without wishing to be limited by the scientific aspect, it appears indeed that the texturing polysaccharides are involved in the capacity of the coating to properly adhere to the ice cream and to be at the same time flexible and crunchy.

The coating may thus comprise 1% to 70% of a milk fermented by the lactic acid bacteria (and then inactivated), 0.5% to 5% of animal or vegetable proteins, and a fat content of 2% to 20%, it being possible for the said fat to be of lactic origin, it being possible for the said proteins to be egg yolk or whey proteins, for example. It may be noted that it is not necessary to add compounds high in vegetable or nonvegetable fat in order to obtain the fat contents close to 40%, because the texture in the mouth of the frozen coating according to the invention indeed resembles that of a traditional frozen coating having from 40% to 50% vegetable fat, for example.

A dessert perfectly corresponding to the abovementioned conditions may comprise an aerated ice cream portion containing more than $10^6$ cfu/g of lactic acid bacteria, and a coating portion which has been fermented by lactic acid bacteria up to a level of $5 \times 10^6$ cfu/g, and then heat inactivated, and which comprises 0.1% to 10% of a fructooligosaccharide, 1% to 60% of a milk, 0.5% to 5% of animal or vegetable proteins, a sucrose content of 15% to 30% and a lactic fat content of 2% to 20%, for example.

The dessert may thus be provided in the form of a coated frozen lolly, that is to say which has a stick for holding in its center. The aerated ice cream portion of the lolly will be formed according to the moulding or extrusion technique, for example. The lolly may have a polygonal, for example a rectangular, triangular or square, shape, a star shape and the like, or an elliptical or circular shape, for example.

In a second embodiment of the invention, the edible support may be a bakery item, for example a wafer, a biscuit and/or a sponge cake having the shape of a cone or a sheet in which, on which, or between which, the ice cream may be placed. The frozen dessert may therefore have the shape of an ice cream cone, of an ice cream sandwich, a filled cigarette, an ice cream turnover, a filled pancake or an ice cream cake, for example.

Persons skilled in the art have available numerous paste compositions intended to be combined with an ice cream in the context of the preparation of a frozen dessert. As a guide, the wafer or biscuit compositions, and/or the techniques for manufacturing them, which are described in FRI454750, U.S. Pat. No. 3,793,938, U.S. Pat. No. 4,624,855, WO95/32630, U.S. Pat. No. 4,761,293 and GB2167934, are perfectly adaptable by persons skilled in the art, and are therefore incorporated by reference into the description of the present invention.

In the preferred cases, the bakery item is coated on the side in contact with the ice cream with a fine layer of fat coating, for example chocolate, acting as barrier against the influence of moisture and of the lactic acid bacteria.

The subject of the invention is also the combined use of lactic acid bacteria and prebiotic fibers, for the preparation of a frozen composition in which the lactic acid bacteria and the fibers are not substantially in contact, for the treatment and/or the prevention of gastrointestinal disorders, for strengthening the human immune system, or for increasing the absorption of minerals.

This composition may be one of the frozen desserts described above, or even a mixture of prebiotic fibers and encapsulated lactic acid bacteria, dried or otherwise, for example. It has in fact been found that the micro-encapsulation of the bacteria has undeniable technological and therapeutic advantages. First, the micro-encapsulation significantly increases the survival of the lactic acid bacteria, and therefore the number of live lactic acid bacteria which arrive in the intestine. Even more importantly, the lactic acid bacteria are gradually released into the intestine, which allows a prolonged action of the lactic acid bacteria.

Preferably, to encapsulate the lactic acid bacteria, the lactic acid bacteria are freeze-dried or spray-dried (EP96201922.0), and they are incorporated into a gel consisting, for example, of a solidified fatty acid, a sodium alginate, polymerized hydroxypropylmethylcellulose or polymerized polyvinylpyrrolidone. To this effect, the teaching given in FR2443247 (Société des Produits Nestlé) is incorporated by reference into the description of the present invention.

The gastrointestinal disorders may be of various types, generally linked to a poor balance in the intestinal flora, which may thus lead to problems of constipation and diarrhea. It is also known that the human immune system is particularly sensitive to the compounds produced by the lactic acid bacteria. The *Lactobacillus johnsonii* strain CNCM I-1225 is in this regard an ideal candidate for fulfilling the needs of the present invention. Moreover, it is now also known that lactic acid bacteria may be directly involved in the facilitated absorption of minerals such as calcium, magnesium, iron and/or zinc, for example (see EP97111380.8, Société des Produits Nestlé).

The present invention is described in greater detail by the examples presented below. It goes without saying, however, that these examples are given by way of illustration of the subject of the invention and do not constitute in any manner a limitation thereto. The percentages are given by weight unless otherwise indicated. In these examples, the strains *Lactobacillus johnsonii* LA-1, *Bifidobacterium longum* Bl16 and *Streptococcus thermophilus* Sfi21 were respectively deposited, solely by way of example, on Jun. 30, 1992 (La-1 and Bl16) and on May 18, 1994 (Sfi21), at the Collection Nationale de Cultures de Microorganismes (CNCM), 25 rue du docteur Roux, 75724 Paris, France, where they received respectively the deposit numbers CNCM I-1225, CNCM I-1228 and CNCM I-1424.

EXAMPLE 1

Aerated Ice Cream with Addition of Fermented Milk

A concentrated ice cream base is prepared by mixing at 60–65° C. for 20 min about 11% of lactic fat, 8.8% of milk solids (not fat), 25% sucrose, 5% of glucose syrup and 0.6% of Emulstab® SE30. The base is homogenized at 72–75° C. and at 210 bar (2 stages at 210/50 bar), it is pasteurized at 85° C. for 22 sec (APV pasteurizer, France, Evreux, 400/h), it is cooled to 4° C., and 40% of a milk acidified by the strains *Lactobacillus johnsonii* La-1 ($10^7$ cfu/ml) and *Bifidobacterium longum* Bl16 ($10^7$ cfu/ml) is added thereto. The composition of the cream thus prepared is presented in Table 1 below.

TABLE 1

| Ingredients | Composition (kg) | Fat (%) | Solids-not-fat (%) | Sucrose (%) | Dry extract (%) |
|---|---|---|---|---|---|
| Cream (35%) | 31.43 | 11.00 | 1.57 | | 12.57 |
| Skimmed milk powder | 7.60 | | 7.30 | | 7.30 |
| Sucrose | 36.77 | | | 25.00 | 25.00 |
| Glucose syrup | 5.27 | | | | 5.00 |
| Emulstab ® SE30 | 0.67 | | | | 0.63 |
| Water | 18.26 | | | | |
| Total: cream base | 100.00 | 11.00 | 8.87 | 25.00 | 50.50 |
| Cream base (60%) | 60.00 | 6.60 | 5.32 | 15.00 | 30.30 |
| Acidified milk (40%) | 40.00 | 1.40 | 4.68 | — | 6.08 |
| Total: cream base + acidified milk | 100.00 | 8.00 | 10.00 | 15.00 | 36.38 |

After maturation of the cream for 12 h at 4° C., it is frozen to an overrun of 95% by volume (Crepaco freezer, France, Evreux; 160 l of product/h), and then all or part of the aerated cream is coated with the various coating compositions described below.

To prepare a moulded bar, the conventional technique of "shell and core" filling is used. To this effect, the coating, whose composition is given in Table 2 below, is measured out into a mould, the said mould being placed in a glycol-containing water bath at −35° C. After 30 s, the non-frozen coating is aspirated, only the frozen coating remains in the mould, to form a shell. The ice cream aerated to an overrun of 95%, coming out of the freezer at −3° C., is then measured out into this shell. After waiting for 30 min, the bar is unmoulded. It is then sprayed with spring water, packaged, placed for 3 hours in a hardening chamber at −40° C. and then stored in a chamber at −30° C.

TABLE 2

| Ingredient | Weight (g) | Supplier |
|---|---|---|
| Condensed milk 9% fat | 30.7 | |
| Liquid sugar 68% dry matter | 4.78 | |
| Fructooligosaccharide Actilight ® 950P | 10 | Beghin Meiji, FR |
| Invert sugar syrup 2/3 | 9.28 | |
| Atomized glucose syrup 36/40 | 6.56 | |
| Modified maize starch H Colflo ® 67 | 1.1 | National Starch, US |
| LGC450 | 1.5 | New Zealand Milk Product, NZ |
| Tartaric acid | 0.145 | |
| Lemon sauce 98/21 | 0.8 | Ciprial, FR |
| Pasteurized cream containing 35% fat | 33.6 | |
| Water | 1.535 | |
| Total: BASE | 100 | |
| BASE | 60 | |
| Acidified milk | 40 | |
| TOTAL | 100 | |

To prepare an extruded bar, ice cream aerated to an overrun of 95%, coming out of the freezer at −5° C./−6° C., is extruded with an extruder having an extrusion head of the desired shape. The extruded bar is then frozen in a freezing tunnel at −45° C. The bar is then coated by dipping into the composition presented in Table 3 below. It is then sprayed with spring water, packaged, placed for 3 hours in a hardening chamber at about −40° C. and then stored in a chamber at −30° C.

TABLE 3

| Ingredient | Weight (g) | Supplier |
|---|---|---|
| Condensed milk 9% fat | 20.91 | |
| Liquid sugar 68% dry matter | 2.98 | |
| Galactooligosaccharide P7L | 6.42 | Snow Brand Milk Product, JP |
| Invert sugar syrup 2/3 | 4 | |
| Atomized glucose syrup 36/40 | 3.97 | |
| Modified maize starch H Colflo ® 67 | 0.9 | National Starch, US |
| LGC450 | 1.5 | New Zealand Milk Product, NZ |
| Tartaric acid | 0.09 | |
| Lemon sauce 98/21 | 0.5 | Ciprial, FR |
| Pasteurized cream containing 35% fat | 21 | |
| Water | 37.71 | |
| Total: BASE | 100 | |
| BASE | 60 | |
| Acidified milk | 40 | |
| TOTAL | 100 | |

To prepare a pot of ice cream, ice cream aerated to an overrun of 95%, coming out of the freezer at −5° C./−6° C., is extruded with an extruder having an extrusion head of the desired shape, in 12 cl pots. The decoration, whose composition is described in Table 4 below, is measured out and deposited at the surface of the aerated ice cream. The pot is placed for 3 hours in a hardening chamber at about −40° C. and it is then stored in a chamber at −30° C.

TABLE 4

| Ingredient | Weight (g) | Supplier |
|---|---|---|
| Condensed milk 9% fat | 20 | |
| Liquid sugar 68% dry matter | 2 | |
| Fructooligosaccharide Raftilose ® L60 | 6.45 | Raffinerie Tirlemontoise, BE |
| Invert sugar syrup 2/3 | 3 | |
| Atomized glucose syrup 36/40 | 2 | |
| Modified maize starch H Colflo ® 67 | 4 | National Starch, US |
| Liquid egg yolk | 26.7 | Ferme Du Pré |
| Tartaric acid | 0.09 | |
| Lemon sauce 98/21 | 0.5 | Ciprial, FR |
| Water | 35.26 | |
| Total: BASE | 100 | |
| BASE | 60 | |
| Acidified milk | 40 | |
| TOTAL | 100 | |

The ice cream bars and the pots are subjected to successive temperature cycles spread over 24 h, corresponding to steps at −10° C., −20° C. and −30° C., and then at −30° C., −20° C. and −10° C. The ice cream is then subjected to accelerated ageing. The survival of the bacteria over time is then analysed, as well as the stability of the prebiotic fibres. In all the desserts, only a slight decline, of the order of 20%, in the number of lactic acid bacteria is observed after 3 months of accelerated ageing. The prebiotic fibres are also perfectly stable under these conditions.

Finally, the capacity of the coated bars to promote the development of the lactic acid bacteria La-1 and Bl16 in the intestine is also demonstrated by determining the number of La-1 and Bl16 living in the faeces after several days following regular consumption of about 200 ml, that is to say about 100 g, of ice cream per day, and this with respect to a diet free of fibre.

EXAMPLE 2

Aerated and Fermented Ice Cream

A cream is prepared containing 10.8% of lactic fat, 13.5% of milk solids (not fat), 0.3% of Emulstab® SE30, and 0.3% of Emulstab® foam (Grindsted, DK), it is pasteurized at 105° C. for 20 s, it is homogenized at 75° C. and 300 bar, it is cooled to 38° C., and it is inoculated with precultures in MRS medium, taken at the exponential growth phase, in an amount of 5% by weight of an La-1 preculture, and 0.5% by weight of a preculture of Streptococcus thermophilus Sfi21 strain. The cream is then fermented for 10 h at 38° C. until a pH of about 4.5 is obtained. At the end of the fermentation, sucrose and a glucose syrup are added thereto. The composition of the cream is presented in Table 5 below.

TABLE 5

| Ingredients | Composition (kg) | Fat (%) | Solids-not-fat (%) | Sucrose (%) | Dry extract (%) |
|---|---|---|---|---|---|
| Cream (35%) | 30.83 | 10.79 | 1.54 | | 12.33 |
| Skimmed milk powder | 12.45 | | 11.95 | | 11.95 |
| Emulstab ® SE30 | 0.41 | | | | 0.37 |
| Emulstab ® foam | 0.41 | | | | 0.36 |

TABLE 5-continued

| Ingredients | Composition (kg) | Fat (%) | Solids-not-fat (%) | Sucrose (%) | Dry extract (%) |
|---|---|---|---|---|---|
| Water | 55.91 | | | | |
| Total: cream base | 100.00 | 10.79 | 13.49 | — | 25.01 |
| Cream base | 74.14 | 8.00 | 10.00 | — | 18.54 |
| Sucrose | 22.06 | | | 15.00 | 15.00 |
| Glucose syrup | 3.80 | | | | 3.00 |
| Fermented ice cream | 100.00 | 8.00 | 10.00 | 15.00 | 36.54 |

The mixture is then mixed, cooled to 4° C., stored at 4° C., frozen to an overrun of 95% by volume (Crepaco freezer, France; 160 l of product/h), and then coated according to the methods described in Example 1 with the various coating compositions described in this example, or with the egg-containing "shell and core" coating composition given in Table 6 below.

TABLE 6

| Ingredient | Weight (g) | Supplier |
|---|---|---|
| Condensed milk 9% fat | 20 | |
| Liquid sugar 68% dry matter | 3 | |
| Soya bean oligosaccharides | 6.45 | The Calpis Food Ind., JP |
| Invert sugar syrup 2/3 | 4 | |
| Atomized glucose syrup 36/40 | 4.2 | |
| Modified maize starch H Colflo ® 67 | 0.8 | National Starch, US |
| Liquid egg yolk | 25.7 | Ferme Du Pré |
| Tartaric acid | 0.09 | |
| Lemon sauce 98/21 | 0.5 | Ciprial, FR |
| Water | 35.26 | |
| Total: coating | 100 | |

After hardening, the number of live La-1 in the whipped ice creams is of the order of $7 \times 10^6$ cfu/g, and after storing for 3 months at −30° C. of the order of $6 \times 10^6$ cfu/g.

The ice cream bars and the pots subjected to accelerated ageing as described in Example 1 survive particularly well since less than 50% of the lactic acid bacteria die. The prebiotic fibres also remain stable under these conditions.

The capacity of the cooling to adhere to the ice cream and to be flexible and crunchy is also evaluated by a taste panel. The results show that the coated bars exhibit, after one month of accelerated ageing, no adverse changes as regards adherence, flexibility and crunchiness.

Finally, the capacity of the coated bars to promote the development of lactic acid bacteria in the intestine is also demonstrated by determining the number of lactic acid bacteria present in the faeces after several days following regular consumption of about 200 ml of ice cream per day, and this with respect to a diet free of fibre.

EXAMPLE 3

Encapsulation of Lactic Acid Bacteria 80 l of culture medium having the following composition are prepared in a 100 l tank: 0.25% of yeast extract, 1.00% of trypticase, 0.50% of phytone, 1.5% of glucose, 0.05% of L-cysteine-HCl, 0.25% of $K_2HPO_4$, 0.025% of $ZnSO_4$, traces of $FeCl_3$, and the remainder being water.

The culture medium is inoculated with 1 l of a 20 h culture of *Bifidobacterium longum* CNCM-1228. The medium is incubated for 12 h at 30° C. The culture broth is centrifuged and 240 g of cells are harvested. They are diluted in 250 ml of skimmed milk supplemented with 7% lactose. The mixture is frozen in liquid nitrogen. It is freeze-dried at 40° C. overnight. A 5% dispersion of the powder obtained is prepared in hydrogenated vegetable fat having a melting point of 42° C. and liquefied at 45° C. The dispersion is injected at 45° C. at a pressure of 4 bar, at the same time as liquid nitrogen, in an amount of 1 part of dispersion per 5 parts of nitrogen, at the top of a vertical cylinder 1.5 m in diameter and 10 m in height. At the bottom of the cylinder is placed a vessel containing liquid nitrogen in which microbeads containing bifidobacteria whose diameter varies between 0.1 mm and 0.5 mm are collected. The microbeads are then placed in a fluidized bed and an alcoholic solution at 8% zein is sprayed over the bed in a quantity such that the zein layer formed around the microbeads represents 5% of their weight.

The microbeads are then incorporated into the same ice cream described in Example 1 (see Table 1 above) in an amount of at least $10^5$ cfu/g, the only difference being that the 40% of acidified milk is replaced with simply pasteurized milk. The ice cream is then coated according to one of the techniques described in Example 1.

EXAMPLE 4

Ice Cream Cone

A wafer dough containing 10% of fructooligosaccharide Raftilose® L30 (Raffinerie Tirlemontoise S.A., BE) according to the recipe reproduced in Table 7 is prepared. After baking, the wafer is conventionally in the shape of a cone. After cooling, the inside of the cones is coated by spraying a fatty film, and then the cones are filled with the aerated ice cream described in Example 1. For that, the filling ice cream is prepared at −3° C. so as to have a large number of live La-1 bacteria. The 50 mm flame consists of the aerated ice cream described in Example 1, but prepared at −5° C. so as to facilitate the forming of the flame. For a wafer cone of 11.5 g, there are thus used 90 ml of aerated ice cream (about 45 g), 40 ml of decoration in the shape of a flame (about 20 g) are deposited and 5 g of chocolate (spraying and decoration). In this example, 1.1 g of fibres are provided per ice cream cone.

TABLE 7

| Ingredient | Weight (g) | Supplier |
|---|---|---|
| Ordinary wheat flour 55 | 52 | |
| Starch | 0.2 | |
| Fructooligosaccharide Raftilose ® L30 | 10 | Raffinerie Tirlemontoise S.A., BE |
| Sugar | 27.8 | |
| Fat | 8 | |
| Emulsifier | 1.5 | |
| Salt | 0.5 | |
| Total: wafer recipe | 100 | |

EXAMPLE 5

Ice Cream Russian Cigarette

Tubes made of wafer dough, filled with ice cream to form Russian cigarettes, are prepared. The wafer dough is based on the recipe described in Table 7 above, the only difference being that it contains, in place of Raftilose® L30, 10% of galactooligosaccharide P7L (product not degraded during baking: Snow Brand, Japan). As a guide, before rolling up the freshly baked wafer band, a fine layer of chocolate is deposited by spraying onto the inner face, the wafer band is rolled up to form a continuous tube, the dough tube is filled with the ice cream described in Example 1, the wafer tube is cut up continuously into dough tubes having a desired length, and the ends of the dough tubes are coated with the coating composition presented in Table 3 above and they are refrigerated at −20° C.

EXAMPLE 6

Ice Cream Sandwich

A biscuit dough containing 10% of isomaltooligosaccharide Panorich® is prepared according to the recipe presented in Table 8. The biscuit dough is shaped in a rotary machine. After baking and cooling, the biscuits are filled with the aerated ice cream described in Example 1. For two biscuits of 10.5 g each, 100 ml of aerated ice cream (about 50 g) are deposited. For this example, 2.1 g of fibers are supplied by the sandwich.

TABLE 8

| Ingredient | Weight (g) | Supplier |
| --- | --- | --- |
| Flour | 62 | |
| Sugar | 15 | |
| Isomaltooligosaccharide Panorich ® | 10 | Nihon Shokuhin Kako Co., Japan |
| Cocoa powder | 3.5 | |
| Fat | 8 | |
| Emulsifier | 0.4 | |
| Malt extract | 0.5 | |
| Baking powder | 0.4 | |
| Salt | 0.1 | |
| Vanilla flavour | 0.1 | |
| Total: biscuit recipe | 100 | |

EXAMPLE 7

Ice Cream Roll

An ice cream roll, that is to say a sheet of biscuit coated with a layer of ice cream, is prepared which is rolled up over itself and then refrigerated. The biscuit has the composition described in Table 8 above, the only difference being that it contains about 10% by weight of gentiooligosaccharide Gentose® 80P (Nihon Shokuhin Kako Co., Japan; product not degraded during baking). The ice cream is as described in Example 2.

The above examples are illustrative.

The combined use of lactic acid bacteria and prebiotic fibres, such as in the herein described frozen composition in which the lactic acid bacteria and the fibres are not substantially in contact, is useful for the treatment and/or the prevention of gastrointestinal disorders, for strengthening the human immune system, or for increasing the absorption of minerals.

What is claimed is:

1. A frozen dessert comprising (1) an ice cream that contains lactic acid bacteria, (2) an edible support associated with the ice cream, and (3) an edible barrier disposed between the support and the bacteria, wherein the support and barrier are edible by humans and the support comprises fermentable fibers useful for promoting the growth of the lactic acid bacteria in a human intestinal tract once the support is consumed, the support being substantially free of lactic acid bacteria, and a distinct component from the ice cream, the edible barrier being disposed and having a composition for inhibiting fermentation of the fibers by the bacteria prior to the consumption.

2. The frozen dessert according to claim 1, wherein the fibers comprise vegetable pectins; chito-, fructo-, gentio-, galacto-, isomalto-, manno- or xylo-oligosaccharides; soya bean, *Polymnia sonchifolia*, artichoke, oat, onion or asparagus oligosaccharides.

3. The frozen dessert according to claim 1, wherein the ice cream comprises more than $10^6$ cfu/g of lactic acid bacteria and the ice cream is coated upon part or all of one side of the support.

4. The frozen dessert according to claim 1, wherein the ice cream comprises about $10^7$ cfu/g of lactic acid bacteria and the ice cream is positioned between two sheets of the edible support.

5. The frozen dessert according to claim 1, wherein the dessert comprises between about $10^4$ and about $10^7$ cfu per gram of fiber.

6. The frozen dessert according to claim 1, wherein the ice cream comprises encapsulated lactic acid bacteria.

7. The frozen dessert according to claim 1, wherein the lactic acid bacteria are freeze-dried and are encapsulated in the separation substance comprising solidified fatty acid, sodium alginate, polymerized hydroxypropylmethylcellulose, polymerized polyvinylpyrrolidone, or mixtures thereof.

8. The frozen dessert according to claim 1, wherein the edible support is a non-aerated ice cream coating or a bakery item.

9. The frozen dessert according to claim 8, wherein the support comprises between about 1% to about 60% milk, between about 0.5% to about 5% of animal or vegetable proteins, between about 0.1% to about 10% of fibers, between about 15% to about 30% of sucrose, and between about 2% and about 20% fat, by weight.

10. The frozen dessert according to claim 1, wherein the lactic acid bacteria comprises acidophilic bacteria, bifidobacteria, the species *Lactococcus lactis, Lactobacillus rhamnosus, Lactobacillus fermentum, Lactobacillus brevis, Lactobacillus plantarum, Lactobacillus casei, Lactobacillus delbruckii* sbp. *bulgaricus, Lactobacillus delbruckii* sbp. *lactis, Streptococcus thermophilus* or *Leuconostoc mesenteroides*.

11. The frozen dessert of claim 10, wherein the lactic acid bacteria are capable of adhering to human intestinal cells, thereby inhibiting adhesion to said human intestinal cells by pathogenic bacteria.

12. The frozen dessert according to claim 1, wherein the support comprises fibers that have been partially fermented by lactic acid bacteria, and then pasteurized.

13. The frozen dessert according to claim 1, wherein the support is a bakery item, and further comprising a layer of fat between the support and the ice cream.

14. A process of preparing a frozen dessert containing ice cream containing lactic acid bacteria and an edible support, said process comprising:

preparing an ice cream composition;

admixing a source of lactic acid bacteria to the ice cream composition;

whipping and extruding the ice cream composition, such that the overrun is between about 20% to about 200% by volume;

providing an edible support as a distinct component from the ice cream, wherein the support comprises fermentable fibers capable of promoting the growth of lactic acid bacteria in a human digestive tract, and the support is substantially free of lactic acid bacteria and a distinct component from the ice cream; and placing an edible barrier between the support and the bacteria with the ice cream coated over all or part of and/or placed in, and/or placed between said edible support wherein the fibers are selected and the ice cream and bacteria are combined for inhibiting fermentation of the fibers by the bacteria prior to the consumption.

15. The process of claim 14 wherein the ice cream comprises more than about $10^6$ cfu/g of lactic acid bacteria.

16. The process of claim 14 wherein the ice cream is aerated and/or extruded by a dasher, and wherein the temperature at the outlet of the dasher is about −30° C.

17. The process of claim 14 further comprising:

producing the lactic acid bacteria in microbeads; and micro-encapsulating the microbeads.

18. The process of claim 14 wherein the fibers comprise vegetable pectins; chito-, fructo-, gentio-, galacto-, isomalto-, manno- or xylo-oligosaccharides; soya bean, *Polymnia sonchifolia*, artichoke, onion or asparagus oligosaccharides.

19. The process of claim 14 wherein the fibers comprise:

polymers of α-1,4-D-galactuonic acid having a molecular weight of between 400 kDa;

galacto-oligosaccharides containing a saccharide part consisting of 2 to 5 repeating units of structure {-α-D-Glu-(1→4)-β-D-Gal-(1→6)-};

inulin-oligofructoses extracted from chicory;

oligo-saccharides synthesized from sucrose units which comprise a sucrose part consisting of 2 to 9 repeating units of structure {-α-D-Glu-(1→2)-β-D-Fru-(1→2)-};

malto-oligosaccharides comprising a saccharide part consisting of 2 to 7 repeating untis of sturcture {-α-D-Glu-(1→4)-};

isomaltoses comprising a saccharide part consisting of 2 to 6 repeating units of structure {-α-D-Glu-(1→6)-};

gentio-oligosaccharides comprising a saccharide part consisting of 2 to 5 repeating units of structure {-β-D-Glu-(1→6)-};

xylo-oligosaccharides comprising a saccharide part consisting of 2 to 9 repeating units of structure {-β-D-Xyl-(1→4)-};

an oats concentrate;

or mixtures thereof.

20. The process of claim 14 wherein carbon dioxide, nitrogen, or a mixture thereof are incorporated into the ice cream during whipping.

21. The frozen dessert of claim 1, wherein the edible barrier comprises a separation substance disposed between the ice cream and the bacteria.

22. The frozen dessert of claim 21, wherein the separation substance comprises fat.

23. The frozen dessert of claim 1, wherein the separation substance is coated on the support between the support and the bacteria.

24. The frozen dessert of claim 7, wherein the freeze dried bacteria comprises microbeads that are micro-encapsulated in said separation substance.

25. The frozen dessert according to claim 1, wherein the fibers comprise of an amount of β-glucans.

26. The frozen dessert of claim 1 wherein the fibers comprise:

polymers of α-1,4-D-galactuonic acid having a molecular weight of between 400 kDa;

galacto-oligosaccharides containing a saccharide part consisting of 2 to 5 repeating units of structure {-α-D-Glu-(1→4)-β-D-Gal-(1→6)-};

inulin-oligofructoses extracted from chicory;

oligo-saccharides synthesized from sucrose units which comprise a sucrose part consisting of2 to 9 repeating units of structure {-α-D-Glu-(1→2)-β-D-Fru-(1→2)-};

malto-oligosaccharides comprising a saccharide part consisting of 2 to 7 repeating untis of sturcture {-α-D-Glu-(1→4)-};

isomaltoses comprising a saccharide part consisting of 2 to 6 repeating units of structure {-α-D-Glu-(1→6)-};

gentio-oligosaccharides comprising a saccharide part consisting of 2 to 5 repeating units of structure {-β-D-Glu-(1→6)-};

xylo-oligosaccharides comprising a saccharide part consisting of 2 to 9 repeating units of structure {-β-D-Xyl-(1→4)-};

an oats concentrate;

or mixtures thereof.

* * * * *

UNITED STATES PATENT AND TRADEMARK OFFICE
CERTIFICATE OF CORRECTION

PATENT NO. : 6,399,124 B1
DATED : June 4, 2002
INVENTOR(S) : Lesens et al.

It is certified that error appears in the above-identified patent and that said Letters Patent is hereby corrected as shown below:

<u>Title page,</u>
Item [56], References Cited, OTHER PUBLICATIONS,

Change "Johnson et al.," to -- Fujisawa et al., --;
After "*johnsonii* sp. nov." insert -- and --;
After "Group A3" insert -- (Johnson et al. 1980) with the Type Strain of *Lactobacillus amylovorus* (Nakamura 1981) --;
After "taining syrups and their properties"," insert -- Foods and Food Ingredient Journal of Japan, XP-002051109 --;
Change "Food Science & Technology" to -- Cultured Dairy Products Journal, vol. 25, no. 3, pp. 4-6, 8-9 --; and
Change ",Food Science & Technology" to -- Canadian Dairy, vol. 75, no. 3, p. 10 --.

<u>Column 14,</u>
Line 34, change "1" to -- 21 --.
Line 54, change each occurrence of "sbp." to -- *sbp.* --.

<u>Column 15</u>:
Line 28, change "-30°C" to -- -3°C --.
Line 50, change "untis of sturcture" to -- units of structure --.

<u>Column 16</u>:
Line 40, change "untis of sturcture" to -- units of structure --.

Signed and Sealed this

Twenty-fourth Day of December, 2002

JAMES E. ROGAN
*Director of the United States Patent and Trademark Office*